(12) United States Patent
Tsukada et al.

(10) Patent No.: US 10,137,281 B2
(45) Date of Patent: Nov. 27, 2018

(54) CATHETER FOR TREATMENT OF SINUSITIS

(71) Applicant: TSUKADA MEDICAL RESEARCH CO., LTD., Tokyo (JP)

(72) Inventors: Osamu Tsukada, Nagano (JP); Masamichi Iijima, Nagano (JP); Kengo Kanai, Nagano (JP)

(73) Assignee: Tsukada Medical Research Co., Ltd., Tokyo (JP)

( * ) Notice: Subject to any disclaimer, the term of this patent is extended or adjusted under 35 U.S.C. 154(b) by 0 days.

(21) Appl. No.: 14/779,244

(22) PCT Filed: Sep. 9, 2013

(86) PCT No.: PCT/JP2013/074220
§ 371 (c)(1),
(2) Date: Sep. 22, 2015

(87) PCT Pub. No.: WO2014/147868
PCT Pub. Date: Sep. 25, 2014

(65) Prior Publication Data
US 2016/0038723 A1    Feb. 11, 2016

(30) Foreign Application Priority Data
Mar. 22, 2013  (JP) .................. 2013-060256

(51) Int. Cl.
*A61M 25/10*  (2013.01)
*A61B 17/24*  (2006.01)
(Continued)

(52) U.S. Cl.
CPC ......... *A61M 25/1011* (2013.01); *A61B 17/24* (2013.01); *A61M 1/008* (2013.01);
(Continued)

(58) Field of Classification Search
CPC ....... A61M 25/1011; A61M 2025/2015; A61B 17/24
See application file for complete search history.

(56) References Cited

U.S. PATENT DOCUMENTS

| | | |
|---|---|---|
| 3,516,407 A | 6/1970 | Ruggero |
| 4,102,342 A | 7/1978 | Akiyama et al. |
| | (Continued) | |

FOREIGN PATENT DOCUMENTS

| | | |
|---|---|---|
| CA | 2013323 A1 | 9/1990 |
| EP | 0418391 A1 | 3/1991 |
| | (Continued) | |

OTHER PUBLICATIONS

Extended European Search Report dated Nov. 23, 2016 in corresponding EP Application o. 13 87 8993.
(Continued)

*Primary Examiner* — Nathan R Price
*Assistant Examiner* — Courtney Fredrickson
(74) *Attorney, Agent, or Firm* — Harness, Dickey & Pierce, PLC (57) ABSTRACT

A catheter for treatment of sinusitis capable of causing a space in a further rear (distal side) of a posterior nasal aperture to communicate with external air is provided. The catheter comprises an anterior nasal aperture balloon 33, an anterior nasal aperture balloon air supply lumen 39b for inflating the anterior nasal aperture balloon 33, a posterior nasal aperture balloon 13, a posterior nasal aperture balloon air supply lumen 19b for inflating the posterior nasal aperture balloon 13, and a drainage lumen 39a having an opening 41 between the anterior nasal aperture balloon 33 and the posterior nasal aperture balloon 13, in which an (Continued)

external air communication lumen 19a having an opening 21 on a distal side from the posterior nasal aperture balloon 13 is further provided.

9 Claims, 8 Drawing Sheets (51) Int. Cl.
*A61M 1/00* (2006.01)
*A61M 25/00* (2006.01)
*A61M 25/01* (2006.01)

(52) U.S. Cl.
CPC ............ *A61M 2025/0031* (2013.01); *A61M 2025/0037* (2013.01); *A61M 2025/0078* (2013.01); *A61M 2025/0175* (2013.01); *A61M 2025/1015* (2013.01); *A61M 2025/1052* (2013.01); *A61M 2025/1061* (2013.01); *A61M 2025/1079* (2013.01); *A61M 2210/0618* (2013.01); *A61M 2210/0681* (2013.01)

(56) References Cited

U.S. PATENT DOCUMENTS

| | | | |
|---|---|---|---|
| 5,024,658 A | | 6/1991 | Kozlov et al. |
| 5,304,140 A | | 4/1994 | Kugo et al. |
| 5,484,412 A | * | 1/1996 | Pierpont ............ A61M 25/104 604/101.03 |
| 6,231,543 B1 | * | 5/2001 | Hegde ................... A61M 25/10 604/96.01 |
| 6,669,711 B1 | | 12/2003 | Noda |
| 2002/0169414 A1 | * | 11/2002 | Kletschka ........ A61B 17/22032 604/104 |
| 2004/0039331 A1 | * | 2/2004 | Coppi ............. A61B 17/12045 604/101.04 |
| 2005/0240147 A1 | | 10/2005 | Makower et al. |
| 2006/0212022 A1 | * | 9/2006 | Gellman ........... A61M 25/0097 604/509 |
| 2007/0267011 A1 | | 11/2007 | Deem et al. |
| 2012/0259215 A1 | * | 10/2012 | Gerrans ............. A61M 25/1011 600/435 |
| 2013/0053755 A1 | * | 2/2013 | Kerr ...................... A61L 29/106 604/8 |
| 2014/0066708 A1 | * | 3/2014 | Nimkar ............. A61B 1/00082 600/106 |

FOREIGN PATENT DOCUMENTS

| | | |
|---|---|---|
| JP | S52-081992 A | 7/1977 |
| JP | S64-58263 A | 3/1989 |
| JP | H03-503011 A | 7/1991 |
| JP | H03-504935 A | 10/1991 |
| JP | 2004-008509 A | 1/2004 |
| JP | 2005-253538 A | 9/2005 |
| JP | 2007-537784 A | 12/2007 |
| JP | 2009-538641 A | 11/2009 |
| WO | WO-00-09192 A1 | 2/2000 |
| WO | WO-2005-117755 A2 | 12/2005 |
| WO | WO-2007-137235 A2 | 11/2007 |

OTHER PUBLICATIONS

International Search Report and Written Opinion of the International Searching Authority for PCT/JP2013/074220, ISA/JP, dated Oct. 15, 2013.

\* cited by examiner

CATHETER FOR TREATMENT OF SINUSITIS

CROSS-REFERENCE TO RELATED APPLICATIONS

This application is a U. S. National Stage Application of International Application No. PCT/JP2013/074220, filed Sep. 9, 2013 and published in Japanese as WO/2014/147868 on Sep. 25, 2014. This application claims priority to Japanese Application No. 2013-060256, filed Mar. 22, 2013. The disclosures of the above applications are incorporated herein by reference.

TECHNICAL FIELD

The present invention relates to a catheter for treatment of sinusitis and particularly to a catheter for treatment of sinusitis provided with two balloons used for treatment of sinusitis.

BACKGROUND ART

Sinusitis is an inflammation caused in a paranasal sinus. The paranasal sinus refers to cavities covered by mucosa located at four spots, that is, both sides of the nose, between the eyes, and above the eyebrows, and a state in which the inflammation in the nasal cavity reaches the paranasal sinus is the sinusitis. If the sinusitis develops, a swelling or a pain is caused in the paranasal sinus or yellow or green pus comes out of the nose in some cases. The causes can be, for example, the person's natural skeletal system in which pus tends to collect in the paranasal sinus or genetic factors.

Treatment of the sinusitis is given mainly with the purpose of drainage of a secretion such as pus collecting in the paranasal sinus and ventilation of the paranasal sinus. Methods for draining the secretion include Proetz displacement method. The Proetz displacement method is a method of suctioning and removing accumulated matters (which cannot be drained as if a flask with a small amount of water therein is stood upside down) collecting in the paranasal sinus by applying a negative pressure/positive pressure. Actually, a subject is made to assume a supine position, and physiological saline or the like is poured into the nasal cavity on the affected side in a state with the patient's head down. By repeating an operation in which the wing of the nose on an unaffected side is pressed with a finger, a negative pressure is applied to the nasal cavity on the affected side while the patient vocalizes a sound such as "Ah" and then, a positive pressure is applied, the secretion in the paranasal sinus is gradually suctioned and mixed with the physiological saline or the like, viscosity thereof is lowered, and the secretion is gradually excreted.

Figure 9:
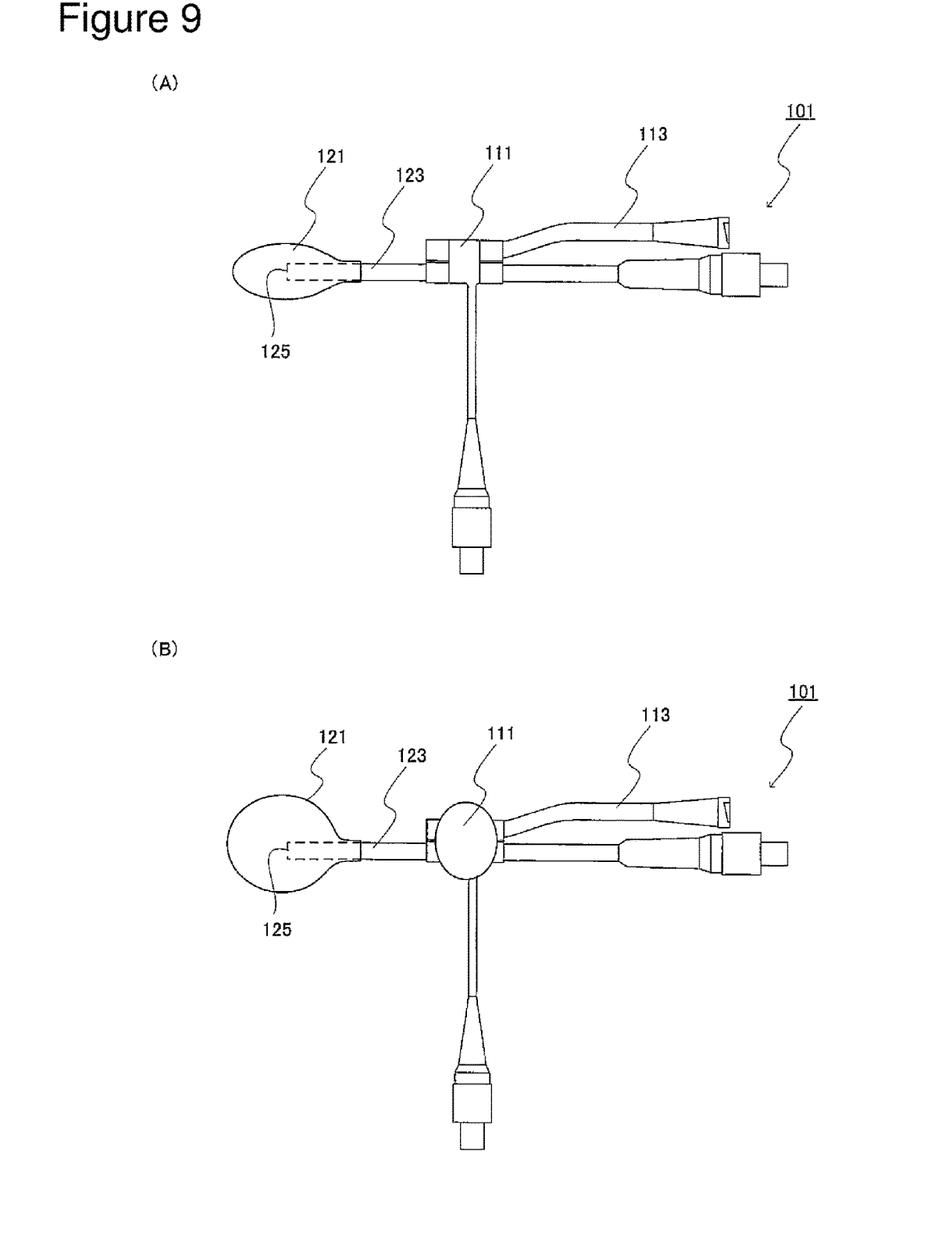

However, the Proetz displacement method has a limitation in its means, and its treatment is mainly for an ethmoidal sinus because of the anatomical position and has a low effect on other sinuses. In order to solve this problem, a catheter 101 for treatment of sinusitis as illustrated in FIG. 9 has been developed as a catheter capable of freely suctioning pus in all the paranasal sinuses. The catheter 101 for treatment of sinusitis is provided with two balloons 111 and 121. Specifically, the catheter 101 for treatment of sinusitis is inserted into the nose, and the two balloons 111 and 121 are inflated in front of and behind a natural opening open in the nasal cavity so as to block the inside of the nasal cavity. A drainage catheter 113 is provided in the catheter 101 for treatment of sinusitis, and a syringe (not shown) is connected to the drainage catheter 113, and a piston of the syringe is pushed/pulled. Here, a tip end of the drainage catheter 113, to which the syringe is connected, communicates with the inside of the nasal cavity sandwiched by the two balloons. By means of an action of the piston, a negative pressure is generated in the space sandwiched by the two balloons, and the pus in the paranasal sinus is pulled out of the natural opening.

Cleaning of the inside of the nasal cavity by the catheter 101 for treatment of sinusitis is performed by filling a lavage fluid in the syringe. Since openings of auditory tubes are outside the two balloons 111 and 121, there is no concern that the lavage fluid flows into the middle ear. By also filling antibiotics in the syringe, it can be directly put into the paranasal sinus. Since the catheter 101 for treatment of sinusitis causes a patient less pain and can freely suction the pus in all the paranasal sinuses, it is extremely effective for treatment of acute or chronic sinusitis.

SUMMARY

Technical Problem

However, the prior-art catheter 101 for treatment of sinusitis has the following problems. That is, as illustrated in FIG. 9, the catheter 101 for treatment of sinusitis has the two balloons 111 and 121 provided, but if a side to which the syringe is connected is defined to be a proximal end side and a side opposite to it to be a distal end side, the balloon 121 on the distal end side becomes a posterior nasal aperture balloon and the balloon 111 provided in a middle portion is an anterior nasal aperture balloon. Here, a tip end portion opening 125 of a posterior nasal aperture balloon air supply tube 123 communicates with an internal space of the posterior nasal aperture balloon 121. In other words, it does not reach a further rear of the balloon 121. Thus, the nasal cavity in the further rear of the posterior nasal aperture is completely shut off from external air by the balloon 121. In this state, there are cases in which the posterior nasal aperture balloon 121 further moves to the rear and the balloon 121 is fitted in a respiratory tract and in which communication between the respiratory tract and the external air is completely shut off.

Solution to Problem

The present invention was made in view of the aforementioned problems, and the catheter was fabricated with the purpose of ensuring the respiratory tract during the treatment. For that purpose, first means employs constitution which includes an anterior nasal aperture balloon, an anterior nasal aperture balloon air supply lumen for inflating the anterior nasal aperture balloon, a posterior nasal aperture balloon, a posterior nasal aperture balloon air supply lumen for inflating the posterior nasal aperture balloon, and a drainage lumen having an opening between the anterior nasal aperture balloon and the posterior nasal aperture balloon, in which an external air communication lumen having an opening on a distal side from the posterior nasal aperture balloon is further provided. By employing such constitution, a space in the further rear of the posterior nasal aperture balloon and the external air can be made to communicate with each other. As a result, even if the posterior nasal aperture balloon further moves to the rear of the nasal cavity and is thus fitted in the respiratory tract, the respiratory tract can be made to communicate with the external air.

Moreover, second means employs constitution in which, in addition to the aforementioned constitution, the anterior nasal aperture balloon and the posterior nasal aperture balloon are both formed of silicone rubber. By employing such constitution, even if a catheter for treatment of sinusitis is inserted into the nasal cavity, there is no influence caused by a material to a human body. Moreover, since silicone rubber has higher elasticity than that of latex or the like, the balloon can be inflated with a lower internal pressure. This means that even if the balloon is inflated in the nasal cavity, a pressure applied to a tissue in the nasal cavity can be minimized.

Moreover, third means employs constitution in which, in addition to the aforementioned constitution, the external air communication lumen is provided in the posterior nasal aperture balloon air supply lumen. By employing such constitution, the posterior nasal aperture balloon air supply lumen and the external air communication lumen can be realized by a simple structure.

Moreover, fourth means employs constitution in which, in addition to the aforementioned constitution, the external air communication lumen penetrates the posterior nasal aperture balloon. By employing such constitution, communication between the space in the further rear (distal side) of the posterior nasal aperture balloon and the external air can be realized easily.

Moreover, fifth means employs constitution in which, in addition to the aforementioned constitution, a surface of a tip end portion of the posterior nasal aperture balloon is substantially orthogonal to a longitudinal direction of the posterior nasal aperture balloon air supply lumen. By employing such constitution, even if the catheter for treatment of sinusitis is to be inserted into deeper than a normal position (respiratory tract, for example), since the tip end portion surface of the posterior nasal aperture balloon is orthogonal to the aperture, the catheter is prevented from being inserted deeper.

Moreover, sixth means employs constitution in which, in addition to the aforementioned constitution, the anterior nasal aperture balloon air supply lumen is provided in the drainage lumen. By employing such constitution, the anterior nasal aperture balloon air supply lumen and the drainage lumen can be realized by a simple structure.

Moreover, seventh means employs constitution in which, in addition to the aforementioned constitution, the external air communication lumen and the posterior nasal aperture balloon air supply lumen are provided inside a posterior nasal aperture balloon catheter, and the drainage lumen and the anterior nasal aperture balloon air supply lumen are provided inside a drainage catheter. By employing such constitution, while having a basic structure close to the prior-art catheter for treatment of sinusitis, the external air communication lumen which is one of the features of the present invention can be provided.

Moreover, eighth means employs constitution in which a wire as a contrast member is embedded in at least either one of the posterior nasal aperture balloon catheter and the drainage catheter. By employing such constitution, when the catheter for treatment of sinusitis is to be inserted into the nasal cavity, its insertion position can be easily checked, and positioning at a wrong position can be reliably prevented.

Furthermore, ninth means employs constitution in which a distance between the posterior nasal aperture balloon and the anterior nasal aperture balloon can be adjusted. By employing such constitution, each balloon can be positioned appropriately in accordance with the distance between the posterior nasal aperture and the anterior nasal aperture of a patient.

BRIEF DESCRIPTION OF THE DRAWINGS

FIG. 2 are sectional views in each portion in the catheter for treatment of sinusitis disclosed in FIG. 1, in which FIG. 2A is a view at A-A line in FIG. 1, FIG. 2B is a view at B-B line in FIG. 1, and FIG. 2C is a view at C-C line in FIG. 1.

FIG. 6 are photos of a connector of the catheter for treatment of sinusitis disclosed in FIG. 1, in which FIG. 6A is a photo of the connector seen from a proximal end side, and FIG. 6B is a photo of the connector seen from a side.

FIG. 8 are views illustrating a mechanism for causing a posterior nasal aperture balloon catheter to slide with respect to a drainage catheter, in which FIG. 8A is a partially cutaway sectional view, and FIG. 8B is a view of the drainage catheter seen from a tip end side.

FIG. 9 are entire appearance views illustrating a prior-art catheter for treatment of sinusitis, in which FIG. 9A illustrates a state in which the balloon is deflated, and FIG. 9B illustrates a state in which the balloon is inflated.

DESCRIPTION OF EMBODIMENT

Subsequently, an embodiment of the present invention will be described by referring to the attached drawings. The embodiment is only an example of the present invention, and a scope of rights defined by description of the claims is not limited to the example of this embodiment. Moreover, in this embodiment, a catheter for treatment of sinusitis is explained as a combination of each constituent element. However, the present invention is not limited to the catheter for treatment of sinusitis including all the constituent elements at the same time but its scope of rights includes a catheter for treatment of sinusitis provided with at least one of the constituent elements.

[Entire Outline]

Figure 1:
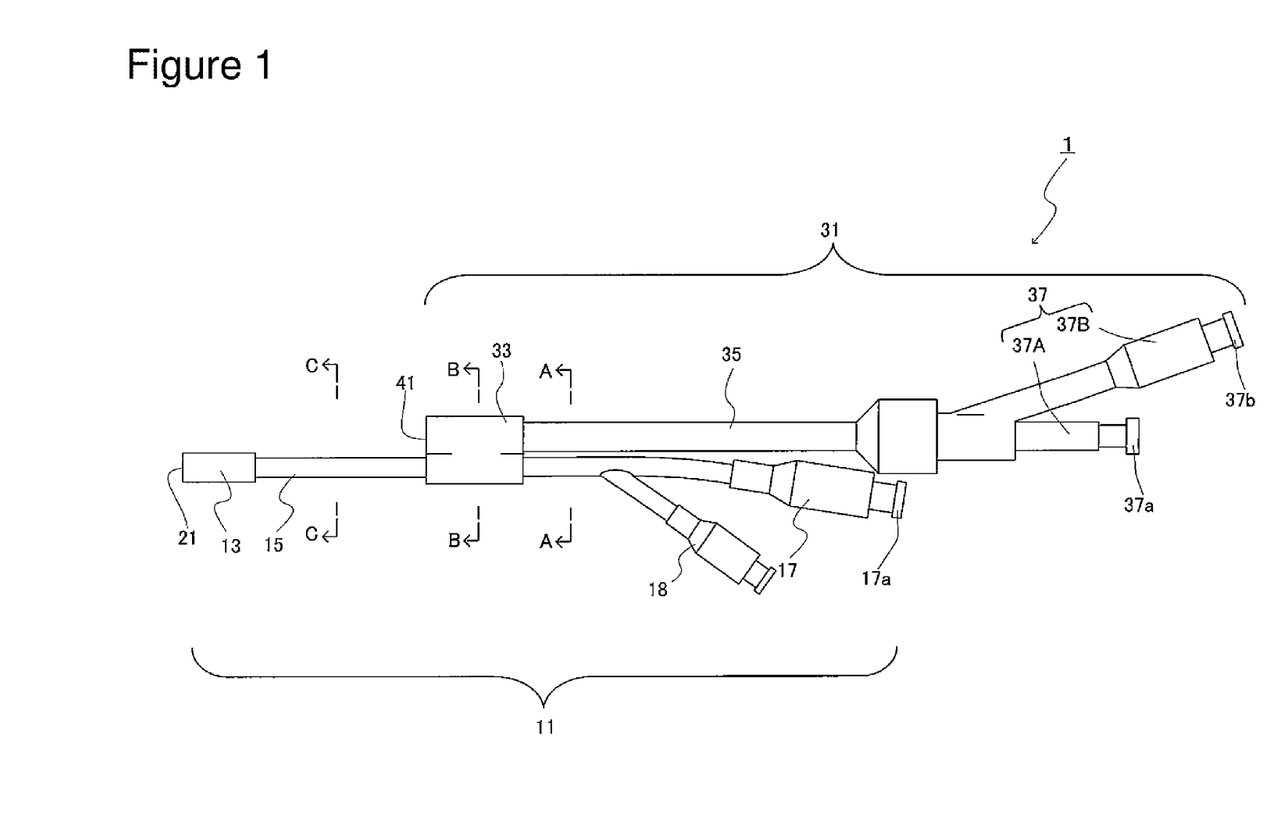
FIG. 1 is a view illustrating an entire appearance of a catheter for treatment of sinusitis according to an embodiment of the present invention.
Figure 2:
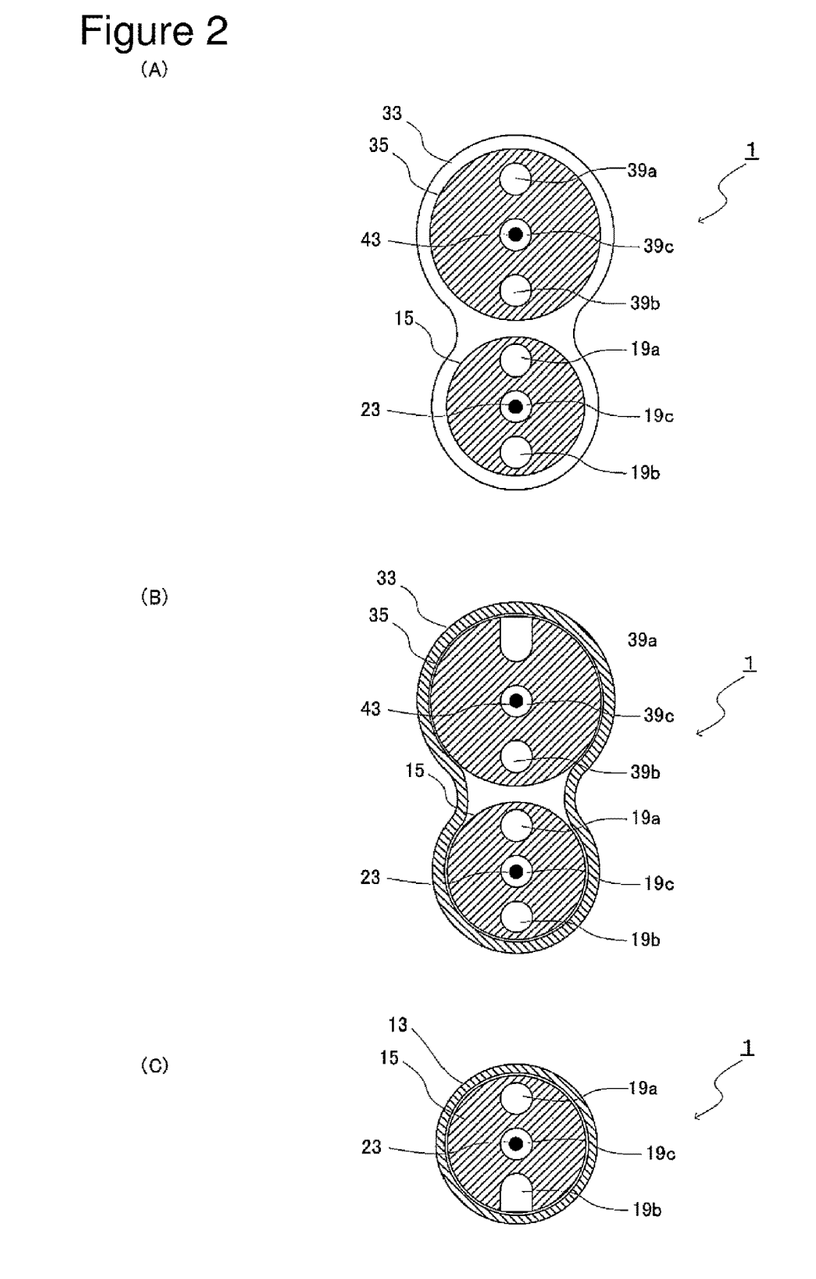

FIG. 1 is an entire appearance view of a catheter 1 for treatment of sinusitis according to this embodiment. FIG. 2 are sectional views illustrating each portion of the catheter 1 for treatment of sinusitis disclosed in FIG. 1, respectively. The catheter 1 for treatment of sinusitis is roughly provided with a posterior nasal aperture balloon catheter 11 and a drainage catheter 31. A tip end portion of the drainage catheter 31 is joined to and integrated with a middle portion of the posterior nasal aperture balloon catheter 11. At a tip end portion of the posterior nasal aperture balloon catheter 11, a posterior nasal aperture balloon 13 is provided. On the other hand, at a tip end portion of the drainage catheter 31, an anterior nasal aperture balloon 33 is provided. Here, expressions of "anterior" and "posterior" are defined such that a proximal side (connector side) of the catheter 1 for treatment of sinusitis is "anterior", while a distal side (tip end side) of the catheter for treatment of sinusitis is "posterior".

[Posterior Nasal Aperture Balloon Catheter]

The posterior nasal aperture balloon catheter 11 includes an elongated body 15, the posterior nasal aperture balloon 13 provided on a distal end of the elongated body 15, and a first connector 17 provided on a proximal end of the elongated body 15. Moreover, in the vicinity of the proximal end of the elongated body 15, an external air communication connector 18 is provided by branching. The elongated body 15 and the posterior nasal aperture balloon 13 are formed of silicone rubber. Inside the elongated body 15, as illustrated in FIG. 2, three lumens 19a, 19b, and 19c are formed. The first lumen is an external air communication lumen 19a communicating from the external air communication connector 18 to an opening 21 on the distal end. The external air communication lumen 19a is a lumen not provided in the prior-art catheter for treatment of sinusitis and is a lumen for the respiratory tract and the external air to communicate with each other even if the posterior nasal aperture balloon 13 is fitted in a respiratory tract. A diameter of each lumen in FIG. 2 is for convenience of explanation and an actual diameter is set appropriately in accordance with the purpose. The same applies to each lumen of the drainage catheter which will be described below.

The second lumen is a posterior nasal aperture balloon air supply lumen 19b. The posterior nasal aperture balloon air supply lumen 19b is for inflating the posterior nasal aperture balloon 13 and allows the first connector 17 on the proximal end and an inside of the posterior nasal aperture balloon 13 to communicate with each other. The posterior nasal aperture balloon air supply lumen 19b is installed outside the aforementioned external air communication lumen 19a but both are formed completely independently. Thus, air communication or the like does not occur between the two.

The third lumen is a contrast member lumen 19c. The contrast member lumen 19c is a lumen for embedding a wire 23 as a contrast member. If sinusitis is to be treated by the catheter 1 for treatment of sinusitis, the catheter 1 for treatment of sinusitis is inserted into the nasal cavity, but in order to enable checking of an insertion position of the catheter 1 for treatment of sinusitis by an X-ray imaging device or the like, the contrast member 23 is embedded. In this embodiment, the wire 23 is used as the contrast member, but the present invention is not limited to this and any member can be employed as long as the member exerts a contrasting action. The contrast member does not necessarily have to be embedded over the entire length of the posterior nasal aperture balloon catheter 11. Moreover, the contrast member is not indispensable in the present invention.

The posterior nasal aperture balloon 13 is provided at a tip end portion of the posterior nasal aperture balloon catheter 11. Specifically, on a distal end of the posterior nasal aperture balloon catheter 11, it is provided in a form so as to surround an outer peripheral portion. Thus, a distal end of the posterior nasal aperture balloon catheter 11 penetrates the posterior nasal aperture balloon 13 and becomes the opening 21. In this point, it is different from the fact that the tip end portion of the prior-art posterior nasal aperture balloon catheter communicates with the inside of the posterior nasal aperture balloon.

The posterior nasal aperture balloon 13 is also formed of silicone rubber and can be inflated by a relatively low pressure as compared with latex rubber. Thus, even in the inflated state, a pressure force to the tissue in the paranasal sinus is small. Moreover, since silicone rubber does not affect human bodies, there is no problem for the treatment of sinusitis. Note that treatment (drainage treatment) time of sinusitis by the catheter 1 for treatment of sinusitis is approximately 10 to 15 minutes, for example.

There can be considered many methods for fixing the posterior nasal aperture balloon 13 to the elongated body 15 of the posterior nasal aperture balloon catheter 11. In this embodiment, it is fixed by adhesion as an example. That is, the posterior nasal aperture balloon 13 formed having a substantially cylindrical shape is disposed on a distal end of the posterior nasal aperture balloon catheter 11. Then, both end portions of the posterior nasal aperture balloon 13 in a longitudinal direction of the posterior nasal aperture balloon catheter 11 are made bonded to an outer peripheral surface of the catheter through an adhesive. The adhesive used here does not affect human bodies, either.

Subsequently, the first connector 17 provided on the proximal end of the posterior nasal aperture balloon catheter 11 will be described. To the first connector 17, a syringe is to be connected, and a syringe connection portion 17A is formed on a proximal end. The syringe connection portion 17A has an inside opening having a tapered shape so that a tapered tip end portion of the syringe is to be fitted therein. The syringe connection portion 17A of this embodiment is not provided with a special lock mechanism or the like, but a lock mechanism may be provided if unexpected removal of the syringe is to be prevented.

An internal space of the first connector 17 has a structure communicating with the aforementioned external air communication lumen 19a and the posterior nasal aperture balloon air supply lumen 19b. However, an opening/closing valve is provided inside the first connector 17. That is for preventing the posterior nasal aperture balloon 13 from being deflated even if the syringe is removed after the posterior nasal aperture balloon 13 is inflated. On the other hand, after the treatment is finished, the posterior nasal aperture balloon 13 needs to be deflated. Thus, the opening/closing valve is constituted to be opened by a predetermined pressure reduction so that the air can be suctioned out of the posterior nasal aperture balloon 13 if the air is suctioned by the syringe. The first connector 17 is constituted by plastic and is mounted on the proximal end of the elongated body 15 by an adhesive.

On the other hand, the external air communication lumen 19a has a structure communicating with the internal space of the external air communication connector 18. That is because the external air communication lumen 19a is for ensuring communication with the external air at all times even if the posterior nasal aperture balloon 13 is fitted in the respiratory tract.

[Drainage Catheter]

Subsequently, the drainage catheter 31 will be described. The drainage catheter 31 includes an elongated body 35, the anterior nasal aperture balloon 33 provided on a distal end of the elongated body 35, and a connector 37 provided on a proximal end of the elongated body 35. The elongated body 35 and the anterior nasal aperture balloon 33 are formed of silicone rubber. Inside the elongated body 35, as illustrated in FIG. 2, three lumens 39a, 39b, and 39C are formed.

The first lumen is the drainage lumen 39a communicating from the connector 37 on the proximal end to the opening 41 on the distal end. The drainage lumen 39a is a major constituent element of treatment of sinusitis and for draining pus stagnating in the paranasal sinus. The drainage lumen 39a penetrates the anterior nasal aperture balloon 33 and has the distal end opening 41 on the further distal side of the anterior nasal aperture balloon 33. In other words, the distal end opening 41 of the drainage lumen 39a is located between the anterior nasal aperture balloon 33 and the posterior nasal aperture balloon 13. That is because, as will be described later, drainage of the pus in the paranasal sinus sealed by the anterior nasal aperture balloon 33 and the posterior nasal aperture balloon 13 is one of the major purposes of the treatment of sinusitis.

The second lumen is the anterior nasal aperture balloon air supply lumen 39b. The anterior nasal aperture balloon air supply lumen 39b is for inflating the anterior nasal aperture balloon 33, and the connector 37 on the proximal end and the inside of the anterior nasal aperture balloon 33 are made to communicate with each other. The anterior nasal aperture balloon air supply lumen 39b is provided in the aforementioned drainage lumen 39a but the two are formed completely independently. Thus, air communication or the like does not occur between the two.

The third lumen is the contrast member lumen 39C. The contrast member lumen 39C is a lumen for embedding the wire 43 as the contrast member. The details are similar to those of the contrast member lumen 19c provided in the posterior nasal aperture balloon catheter 11. However, if the contrast member is embedded in the posterior nasal aperture balloon catheter 11, there is small necessity in embedding the contrast member in the drainage catheter 31. That is because the insertion position of the catheter 1 for treatment of sinusitis can be checked by the contrast member of the posterior nasal aperture balloon catheter 11. On the other hand, by embedding the contrast member in the drainage catheter 31, the contrast member of the posterior nasal aperture balloon catheter 11 can be omitted. That is because, if the insertion position of the drainage catheter 31 is known, the position of the posterior nasal aperture balloon catheter 11 can be also estimated. In summary, the contrast member is not indispensable constitution but if it is provided, it may be provided on either one of the posterior nasal aperture balloon catheter 11 and the drainage catheter 31 or on both.

The anterior nasal aperture balloon 33 is provided at a tip end portion of the drainage catheter 31. Specifically, it is provided on the distal end of the drainage catheter 31 in a form of surrounding the outer peripheral portion. Thus, as described above, the distal end of the drainage catheter 31 penetrates the posterior nasal aperture balloon 33 and becomes the distal end opening 41. The anterior nasal aperture balloon 33 is also formed of silicone rubber. A method for fixing the anterior nasal aperture balloon 33 to the drainage catheter 31 is also adhesion similarly to the case of the posterior nasal aperture balloon 13. The adhesion state is also similar to the case of the posterior nasal aperture balloon 13.

Subsequently, the connector 37 provided on the proximal end of the drainage catheter 31 will be described. To the connector 37, too, the syringe is to be connected, and a syringe connection portion is formed on a proximal end. The connector 37 is bifurcated unlike the first connector 17 of the posterior nasal aperture balloon catheter 11. One second connector 37A is provided on an extension of the elongated body 35, while the other third connector 37B is branched.

On the second and third connectors 37A and 37B, syringe connection portions 37a and 37b are provided, respectively, and the insides thereof are openings having tapered shapes so that tapered tip end portions of the syringes (not shown) are fitted therein. The syringe connection portions 37A and 37B of this embodiment are not provided with a special lock mechanism or the like, but a lock mechanism may be provided if unexpected removal of the syringe is to be prevented.

An internal space of the second connector 37A has a structure communicating with the aforementioned drainage lumen. The syringe is connected to the second connector 37A so that a lavage fluid, a liquid medicine or the like is poured into the paranasal sinus or the lavage fluid, the pus or the like can be drained from inside of the paranasal sinus. No special structure such as an opening/closing valve is provided in the second connector 37A of this embodiment. However, the opening/closing valve or the like may be provided in order to prevent leakage of the lavage fluid, pus or the like.

In the third connector 37B, an opening/closing valve is provided. That is for preventing the anterior nasal aperture balloon 33 from being deflated even if the syringe is removed after the anterior nasal aperture balloon 33 is inflated. On the other hand, after the treatment is finished, the anterior nasal aperture balloon 33 needs to be deflated. Thus, the opening/closing valve is constituted to be opened by a predetermined pressure reduction so that the air can be suctioned out of the anterior nasal aperture balloon 33 when the air is suctioned by the syringe. The connector 37 is constituted by plastic and is mounted on the elongated body 35 by an adhesive.

Figure 3:
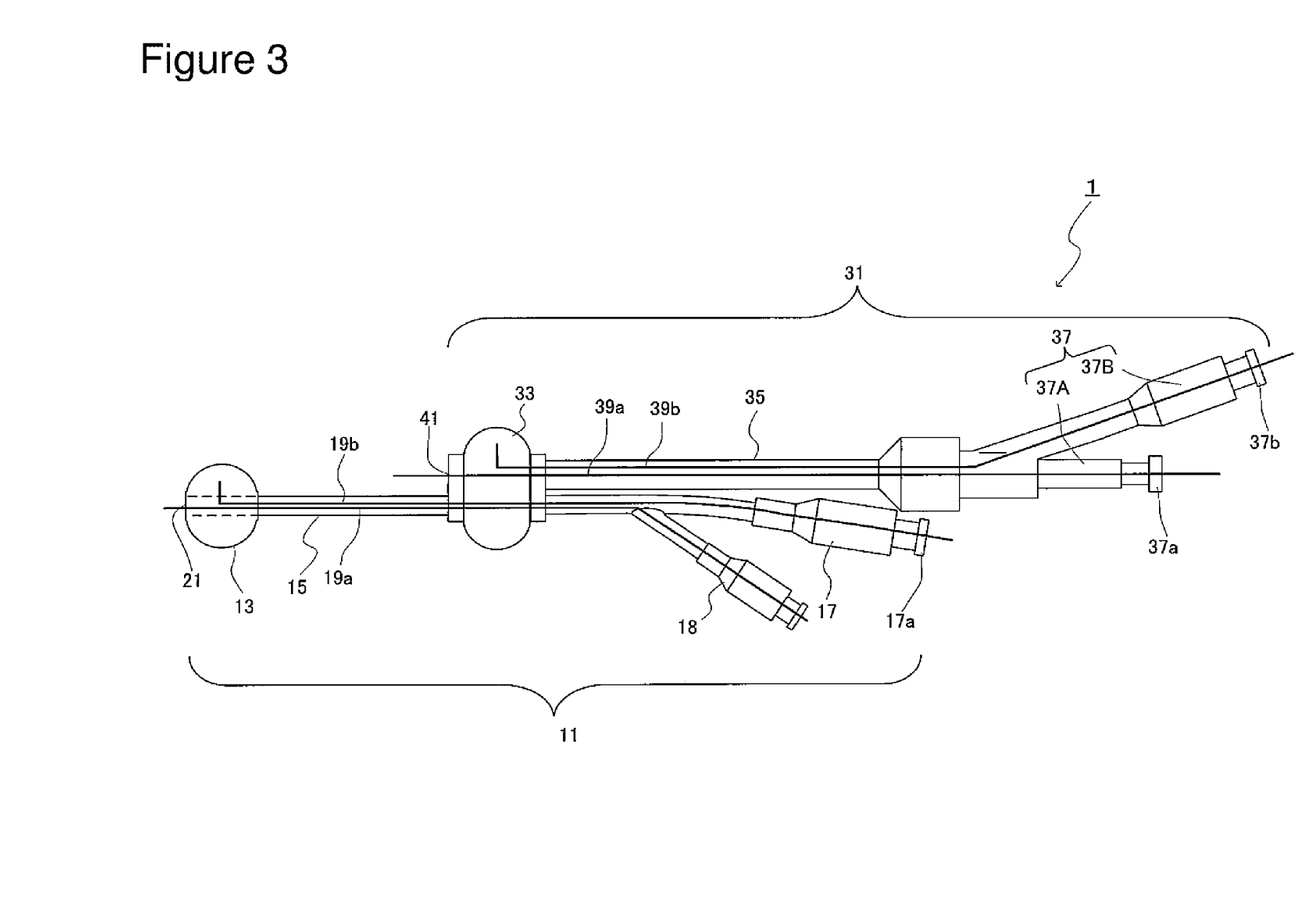
FIG. 3 is a view illustrating the entire appearance of the catheter for treatment of sinusitis disclosed in FIG. 1 in a state in which each balloon is inflated.

Subsequently, a case in which each of the balloons 13 and 33 is inflated in the catheter 1 for treatment of sinusitis of this embodiment will be described on the basis of FIG. 3. In FIG. 3, for convenience of explanation, paths 19a, 19b, 39a, and 39b of the lumens are indicated by bold solid lines. As described above, the posterior nasal aperture balloon 13 communicates with the first connector 17 through the posterior nasal aperture balloon air supply lumen 19b. Thus, by connecting the syringe to the first connector 17 and by pouring the air into it, the posterior nasal aperture balloon 13 is inflated. Here, the shape of the posterior nasal aperture balloon 13 after the inflation has a feature. As illustrated in FIG. 3, the posterior nasal aperture balloon 13 has a substantially spherical shape or a shape slightly crushed in the longitudinal direction of the posterior nasal aperture balloon catheter 11.

The aforementioned shape of the posterior nasal aperture balloon 13 has a purpose. That is, a surface of the balloon in the vicinity of the tip end portion of the posterior nasal aperture balloon catheter 11 is a surface substantially orthogonal to the longitudinal direction of the catheter. With such a shape, even if the posterior nasal aperture balloon 13 is to be fitted in the respiratory tract during the treatment, the posterior nasal aperture balloon 13 is prevented from being fitted in the respiratory tract by the orthogonal surface in some cases.

Moreover, the anterior nasal aperture balloon 33 communicates with the third connector 37B through the anterior nasal aperture balloon air supply lumen 39b. Thus, by connecting the syringe to the third connector 37B and by pouring the air into it, the anterior nasal aperture balloon 33 is inflated. Here, the anterior nasal aperture balloon 33 is inflated around the coupling portion between the posterior nasal aperture balloon catheter 11 and the drainage catheter 31. Thus, if the anterior nasal aperture balloon 33 is inflated in the paranasal sinus, the posterior nasal aperture balloon catheter 11 and the drainage catheter 31 can be positioned close to the center of the paranasal sinus space. However, the structure is an example, and the structure may be such that the posterior nasal aperture balloon catheter 11 and the drainage catheter 31 are located at positions shifted from the centers of the balloons 13 and 33.

Figure 4:
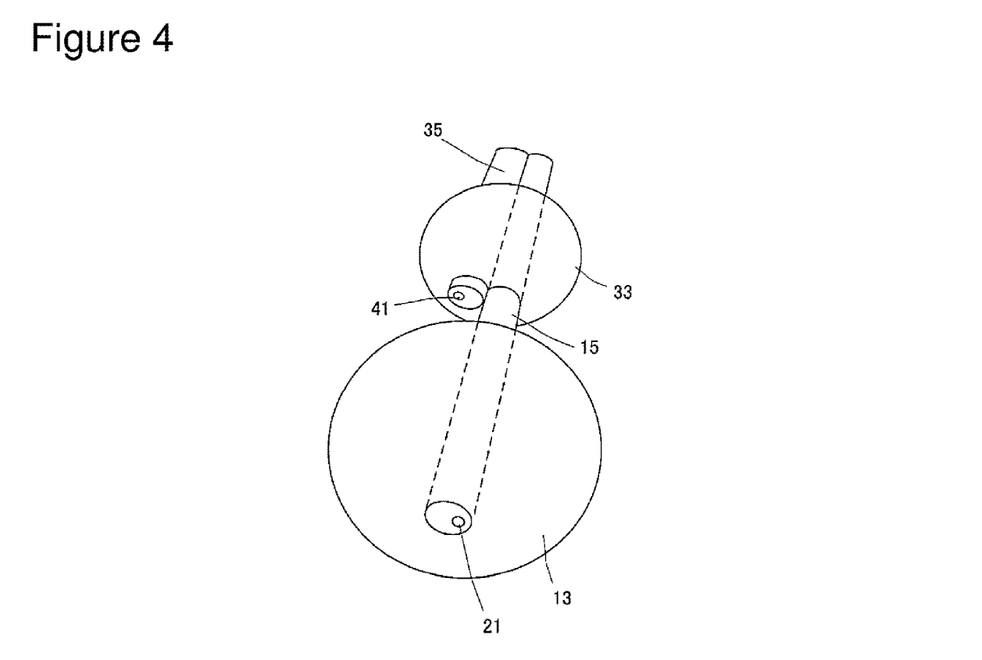
FIG. 4 is a perspective view of the catheter for treatment of sinusitis disclosed in FIG. 1 seen from a side of an opening on a distal end side of an external air communication air supply lumen.
Figure 5:
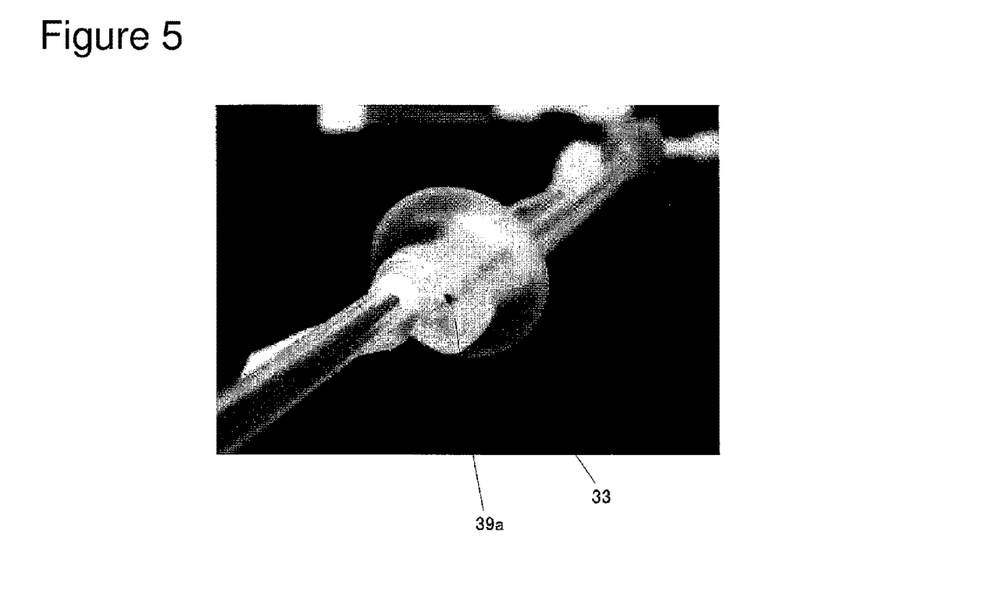
FIG. 5 is a photo of the catheter for treatment of sinusitis disclosed in FIG. 1 seen from a side of an opening on a distal end side of a drainage lumen.

FIG. 4 is a perspective view of the external air communication lumen and the drainage lumen seen from the distal end side of the catheter 1 for treatment of sinusitis. As illustrated in this figure, the distal end side opening 21 of the external air communication lumen is open in substantially the same plane as the surface of the posterior nasal aperture balloon 13. Moreover, the distal end side opening 41 of the drainage lumen is open in a relation so as to slightly protrude from the surface of the anterior nasal aperture balloon 33. FIG. 5 is a photo illustrating the drainage lumen 39*a* and the anterior nasal aperture balloon 33.

Figure 6:
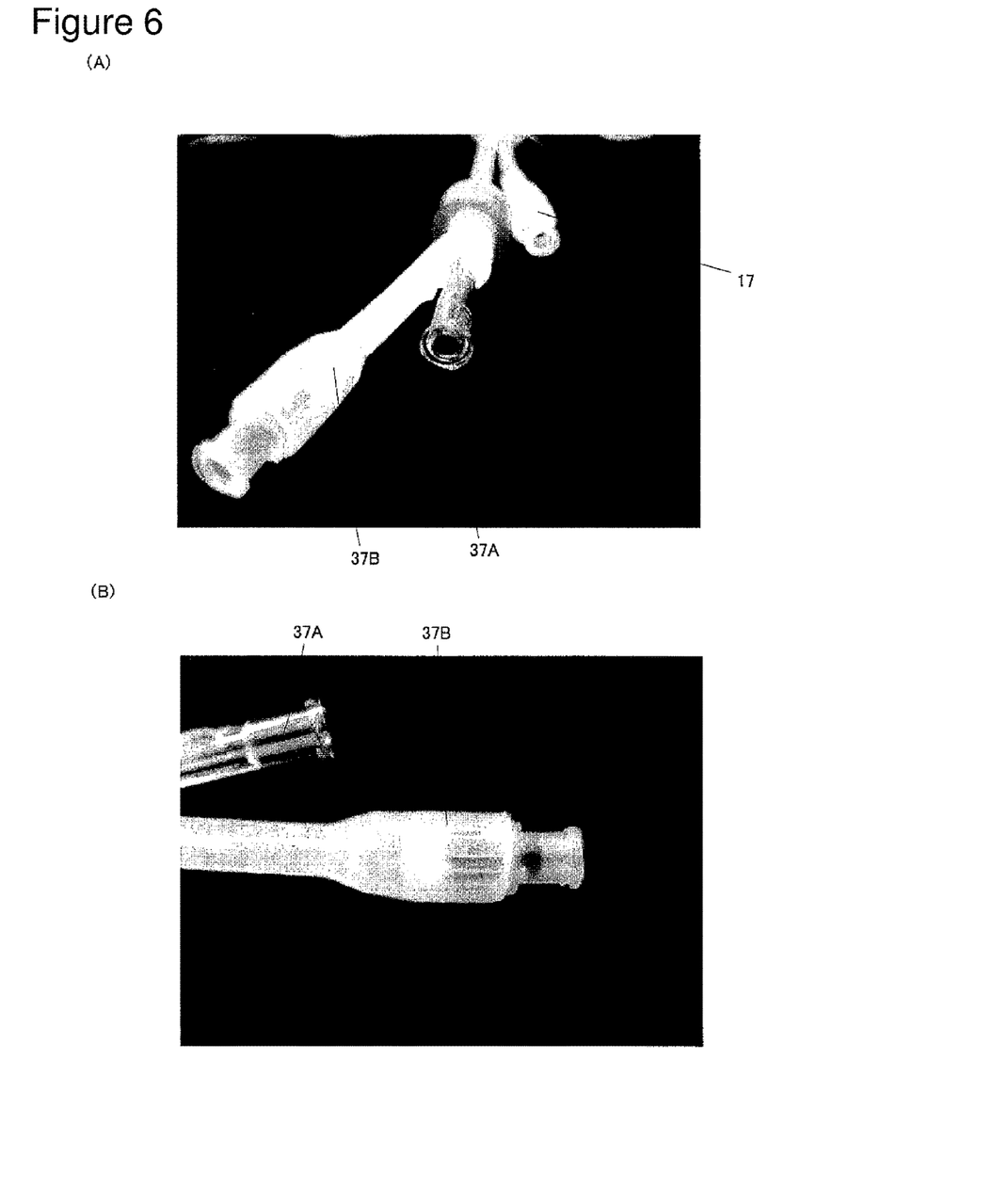

FIG. 6A is a photo of each connector seen from the proximal end side. In this photo, what is seen on the right side is the first connector communicating with the external air communication lumen and the posterior nasal aperture balloon air supply lumen. What is seen at the center portion is the second connector communicating with the drainage lumen. What is seen on the left side is the third connector communicating with the anterior nasal aperture balloon air supply lumen. Moreover, FIG. 6B is an enlarged photo illustrating the second connector and the third connector. Inside the third connector, the aforementioned opening/closing valve is provided.

Figure 8:
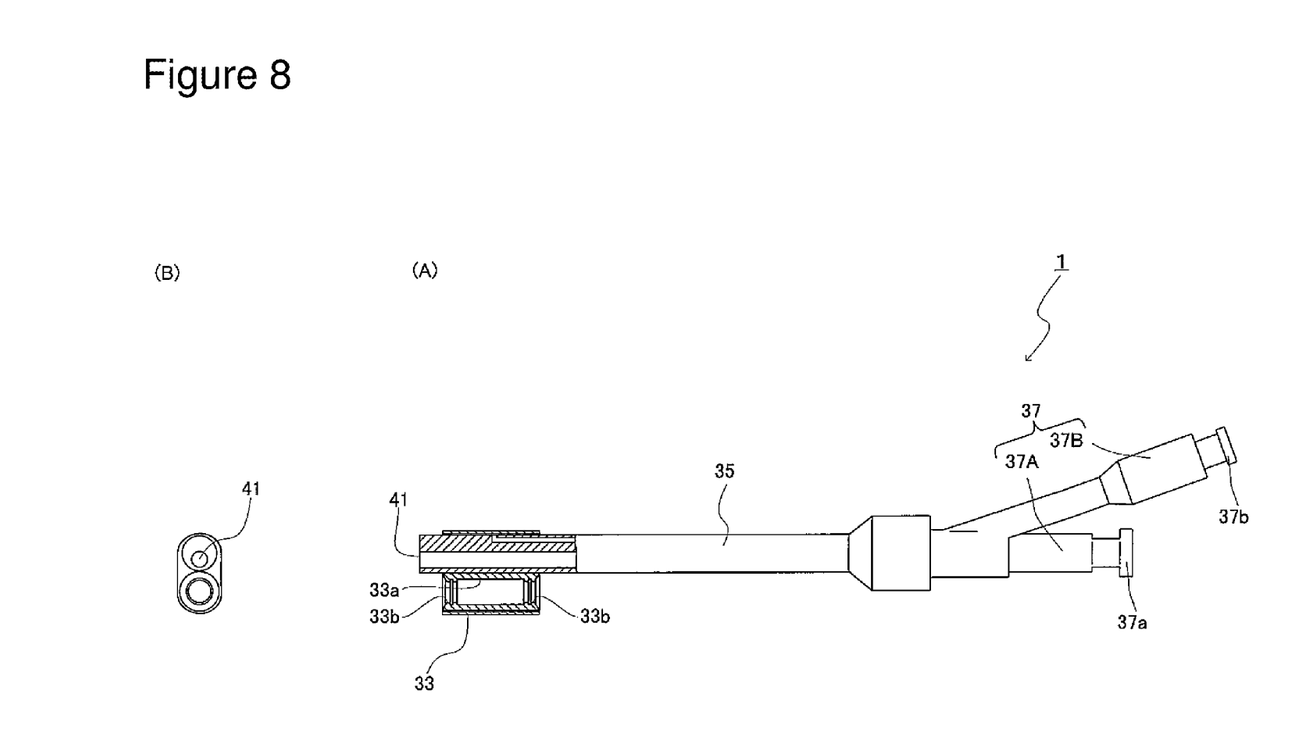

Moreover, a distance between the posterior nasal aperture balloon 13 and the anterior nasal aperture balloon 33 is made adjustable. That is because the distance between the posterior nasal aperture and the anterior nasal aperture is different depending on the patient. As a specific structure, the elongated body 15 of the posterior nasal aperture balloon catheter 11 slides with respect to the distal end of the anterior nasal aperture balloon catheter 31. A slide mechanism is realized by an internal space 33*a* having a circular section formed in the anterior nasal aperture balloon 33 and an annular rib 33*b* formed on an inner surface forming the internal space 33*a* as illustrated in FIG. 8A. The internal space 33*a* is for the posterior nasal aperture balloon catheter 11 to go therethrough. Four ribs 33*b* each having an inner diameter smaller than the inner diameter of the inner surface are provided. The inner diameter of the rib 33*b* is set so as to become smaller than an outer diameter of the posterior nasal aperture balloon catheter 13, and a friction force is generated between the rib 33*b* and the posterior nasal aperture balloon catheter 13. Thus, unintentional movement of the posterior nasal aperture balloon catheter 11 with respect to the drainage catheter 31 can be reliably prevented. At the same time, the rib 33*b* also exerts a sealing function. That is because, in order to take out the pus in the paranasal sinus efficiently by connecting the syringe to the second connector 37A of the drainage catheter and by causing it to perform a piston action so that the inside of the paranasal sinus between the anterior nasal aperture balloon 33 and the posterior nasal aperture balloon 13 is brought into a vacuum state, the sealing function is required. Moreover, the rib can also prevent passage of the pus or the like between the surface of the posterior nasal aperture balloon catheter 11 and the inner surface of the anterior nasal aperture balloon 33. In this embodiment, since four ribs are provided, the sealing function can be exerted more reliably. In the slide mechanism of this embodiment, the four ribs 33*b* are formed two each on both end portions of the internal space 33*a*, but the present invention is not limited to this, and only one rib 33*b* may be provided or two, three or five or more ribs may be provided.

Figure 7:
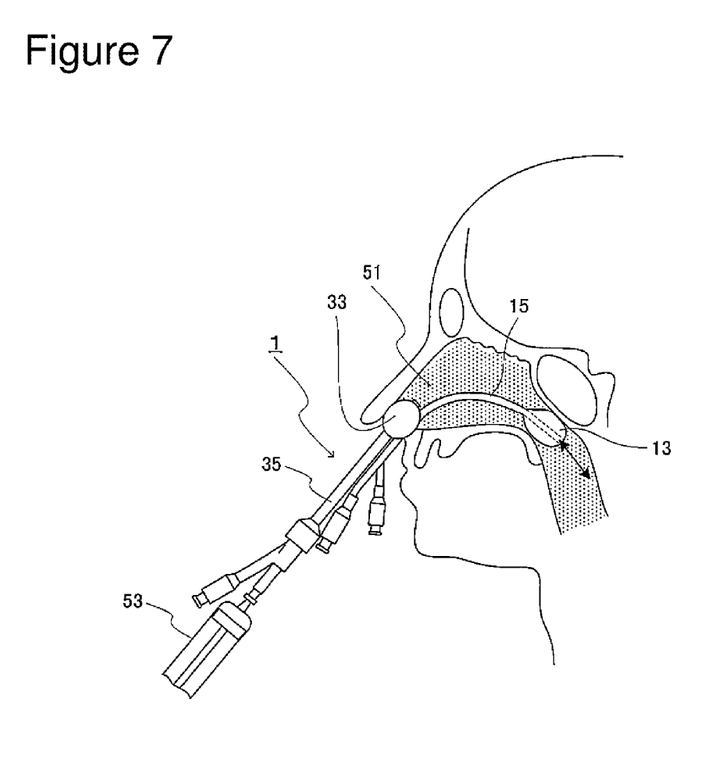
FIG. 7 is a schematic view for explaining a use mode of the catheter for treatment of sinusitis disclosed in FIG. 1.

Subsequently, a use mode of the catheter for treatment of sinusitis according to this embodiment will be described on the basis of FIG. 7. As illustrated in the figure, the catheter 1 for treatment of sinusitis is inserted into the paranasal sinus 51 so that the anterior nasal aperture balloon 33 is positioned in the anterior nasal aperture in the paranasal sinus 51, and the posterior nasal aperture balloon 13 is positioned in the posterior nasal aperture. Positioning of the catheter 1 for treatment of sinusitis is performed while the position of the contrast member is being checked. If it is correctly positioned, the air is supplied to the anterior nasal aperture balloon 33 and the posterior nasal aperture balloon 13 so as to inflate both balloons 13 and 33. In the figure, a state in which each of the balloons 13 and 33 is inflated is illustrated. As a result, the internal space of the paranasal sinus 51 is sealed by the two balloons.

Subsequently, the syringe 53 is connected to the second connector 37A of the drainage catheter 31. The syringe 53 is filled with a liquid used for the treatment of sinusitis such as a lavage fluid or a liquid medicine. Then, the lavage fluid or the like is poured from the syringe 53. The lavage fluid or the like passes through the drainage lumen of the drainage catheter 31 and is ejected from the distal end side opening 41 and poured into the paranasal sinus 51. As a result, the pus in the paranasal sinus 51 and the lavage fluid or the like are mixed, and viscosity of the pus lowers. At this time, since the posterior nasal aperture is sealed by the posterior nasal aperture balloon 13, flowing of the lavage fluid or the like into the middle ear or the like is reliably prevented.

Subsequently, by moving the piston of the syringe 53 to the suction side, the pus which has been softened by the lavage fluid or the like is suctioned. By repeating the pouring-in and suctioning of the lavage fluid or the like as above, the pus in the paranasal sinus 51 can be drained. After drainage of the pus is finished, the anterior nasal aperture balloon 33 and the posterior nasal aperture balloon 13 are deflated and finally, the catheter 1 for treatment of sinusitis is pulled out of the paranasal sinus. As a result, the treatment of sinusitis is finished. Treatment time up to this is approximately 10 to 15 minutes.

INDUSTRIAL APPLICABILITY

The present invention can be used for a catheter for treatment of sinusitis used for the treatment of the paranasal sinus.

REFERENCE SIGNS LIST

1 catheter for treatment of sinusitis
11 posterior nasal aperture balloon catheter
13 posterior nasal aperture balloon
15 elongated body (of posterior nasal aperture balloon catheter)
17 first connector
18 external air communication connector
19*a* external air communication lumen
19*b* posterior nasal aperture balloon air supply lumen
19*c* contrast member lumen (of posterior nasal aperture balloon catheter)
21 distal end side opening (of posterior nasal aperture balloon catheter)
31 drainage catheter
33 anterior nasal aperture balloon
33*b* rib
35 elongated body (of drainage catheter)
37 connector
37A second connector
37B third connector 39a drainage lumen
39b anterior nasal aperture balloon air supply lumen
39C contrast member lumen (of drainage catheter)
41 distal end side opening (of drainage catheter)
51 paranasal sinus
53 syringe

What is claimed is:

1. A catheter for treatment of sinusitis comprising:
an anterior nasal aperture balloon;
an anterior nasal aperture balloon air supply lumen for inflating the anterior nasal aperture balloon;
a posterior nasal aperture balloon;
a posterior nasal aperture balloon air supply lumen for inflating the posterior nasal aperture balloon;
a drainage lumen having an opening between the anterior nasal aperture balloon and the posterior nasal aperture balloon;
a drainage catheter comprising the anterior nasal aperture balloon air supply lumen and the drainage lumen therein;
a posterior nasal aperture balloon catheter comprising the posterior nasal aperture balloon air supply lumen therein; and
an external air communication lumen having an opening on a distal side from the posterior nasal aperture balloon is further provided in the posterior nasal aperture balloon catheter,
wherein the catheter comprising the external air communication lumen is formed of silicone rubber,
wherein the drainage catheter and the posterior nasal aperture balloon catheter are arranged in a side-by-side configuration,
wherein a distance between the posterior nasal aperture balloon and the anterior nasal aperture balloon is adjustable, and
wherein adjustment of the distance between the posterior nasal aperture balloon and the anterior nasal aperture balloon is realized by an internal space having a circular section formed in the anterior nasal aperture balloon through which the posterior nasal aperture balloon catheter passes, and at least one annular sealing rib formed on a wall surface which surrounds the internal space, and the at least one annular sealing rib is configured to seal an annular gap between an outer surface of the posterior nasal aperture balloon catheter and the wall surface such that liquid does not pass through the annular gap between the outer surface and the wall surface.

2. The catheter for treatment of sinusitis according to claim 1, wherein
the anterior nasal aperture balloon and the posterior nasal aperture balloon are both formed of silicone rubber.

3. The catheter for treatment of sinusitis according to claim 1, wherein
the external air communication lumen is provided in parallel with the posterior nasal aperture balloon air supply lumen.

4. The catheter for treatment of sinusitis according to claim 1, wherein
the posterior nasal aperture balloon catheter and the external air communication lumen penetrates the posterior nasal aperture balloon.

5. The catheter for treatment of sinusitis according to claim 1, wherein
a surface of a tip end portion of the posterior nasal aperture balloon is substantially orthogonal to a longitudinal direction of the posterior nasal aperture balloon catheter.

6. The catheter for treatment of sinusitis according to claim 1, wherein
the anterior nasal aperture balloon air supply lumen is provided in parallel with the drainage lumen.

7. The catheter for treatment of sinusitis according to claim 1, wherein
a wire as a contrast member is embedded in at least one of the posterior nasal aperture balloon catheter and the drainage catheter.

8. The catheter for treatment of sinusitis according to claim 1, wherein
a surface of a tip end portion of the posterior nasal aperture balloon is located in substantially same plane as a surface of a tip of the catheter comprising the external air communication lumen.

9. The catheter for treatment of sinusitis according to claim 1, further comprising:
a first connector being in communication with the posterior nasal aperture balloon air supply lumen and configured to connect a syringe to the posterior nasal aperture balloon catheter,
a second connector being in communication with the drainage lumen and configured to connect a syringe to the drainage catheter,
a third connector being in communication with the anterior nasal aperture balloon air supply lumen and configured to connect a syringe to the drainage catheter,
an external air communication connector being in communication with the external air communication lumen.

* * * * *